United States Patent [19]

Pettersen et al.

[11] 3,934,197

[45] Jan. 20, 1976

[54] AUTOMATIC CALIBRATION SYSTEM

[75] Inventors: Aage Pettersen, North Reading; Herbert Schulkind, Natic, both of Mass.

[73] Assignee: Corning Glass Works, Corning, N.Y.

[22] Filed: Dec. 3, 1973

[21] Appl. No.: 420,967

[52] U.S. Cl. ............................. 324/130; 324/30 R
[51] Int. Cl.² .......................................... G01R 1/02
[58] Field of Search ............................. 324/130, 30

[56] References Cited
UNITED STATES PATENTS
3,784,912  1/1974  Aken .................................. 324/130

OTHER PUBLICATIONS

Cohen et al. "Self-Balancing System for Medical and Physiological Instrumentation", IEEE TRANS on Bio-Medical Engineering, Vol. BME–18, No. 1, Jan. 1971.

*Primary Examiner*—R. V. Rolinec
*Assistant Examiner*—Rolf Hille
*Attorney, Agent, or Firm*—Walter S. Zebrowski; Clarence R. Patty, Jr.; Richard E. Kurtz

[57] ABSTRACT

An automatic calibration system for pH meters includes a digital counter and a digital-to-analog converter which produces an output voltage connected to compensate the zero offset DC voltage of the pH measurement system. During a calibration operation a switch is closed to reset the binary counters and to thereafter supply clock pulses to the counters. As these clock pulses are counted, the digital-to-analog converter produces a staircase output voltage. This is applied to one input of a difference amplifier and the measuring voltage of the pH probe is applied to the other input. A detector stops the application of clock pulses to the counter when the staircase voltage equals the DC offset voltage of the pH measuring probe.

2 Claims, 4 Drawing Figures

AUTOMATIC CALIBRATION SYSTEM

BACKGROUND OF THE INVENTION

This invention relates to the automatic calibration of electronic instruments and more particularly to the automatic calibration of a pH measuring system.

In presently available pH meters it is necessary to manually calibrate the instruments for voltage offsets in the electrodes and in the electronics. This is a time consuming job and the accuracy depends upon the operator. The usual manual calibration method includes balancing a high impedance difference amplifier. The operator observes a meter and adjusts the balance until the meter nulls. If more than one calibration point is used, error often results. In making a calibration, it is necessary to set both the slope and the zero offset.

Our copending application Ser. No. 453,794 filed Mar. 22, 1974 is directed to setting the slope of the instrument.

SUMMARY OF THE INVENTION

In accordance with this invention an automatic calibration system for electronic measuring instruments is provided. The system of this invention automatically sets the zero offset calibration. The calibration is easy to perform, accurate and repeatable.

A digital counter has its output connected to a digital-to-analog converter. The output of this converter is a voltage which is algebraically combined with the measuring voltage to compensate for the DC offset in the measuring voltage. During a calibrate operation the counter is initially reset and then counts clock pulses. When the output of the digital-to-analog converter equals the DC offset voltage, a detector stops the counter. The counter accurately retains the correct value necessary to compensate for DC offset during long intervals of time between calibration.

The foregoing and other objects, features and advantages of the invention will be better understood from the following more detailed description and appended claims.

DESCRIPTION OF THE PREFERRED EMBODIMENT

Figure 1:
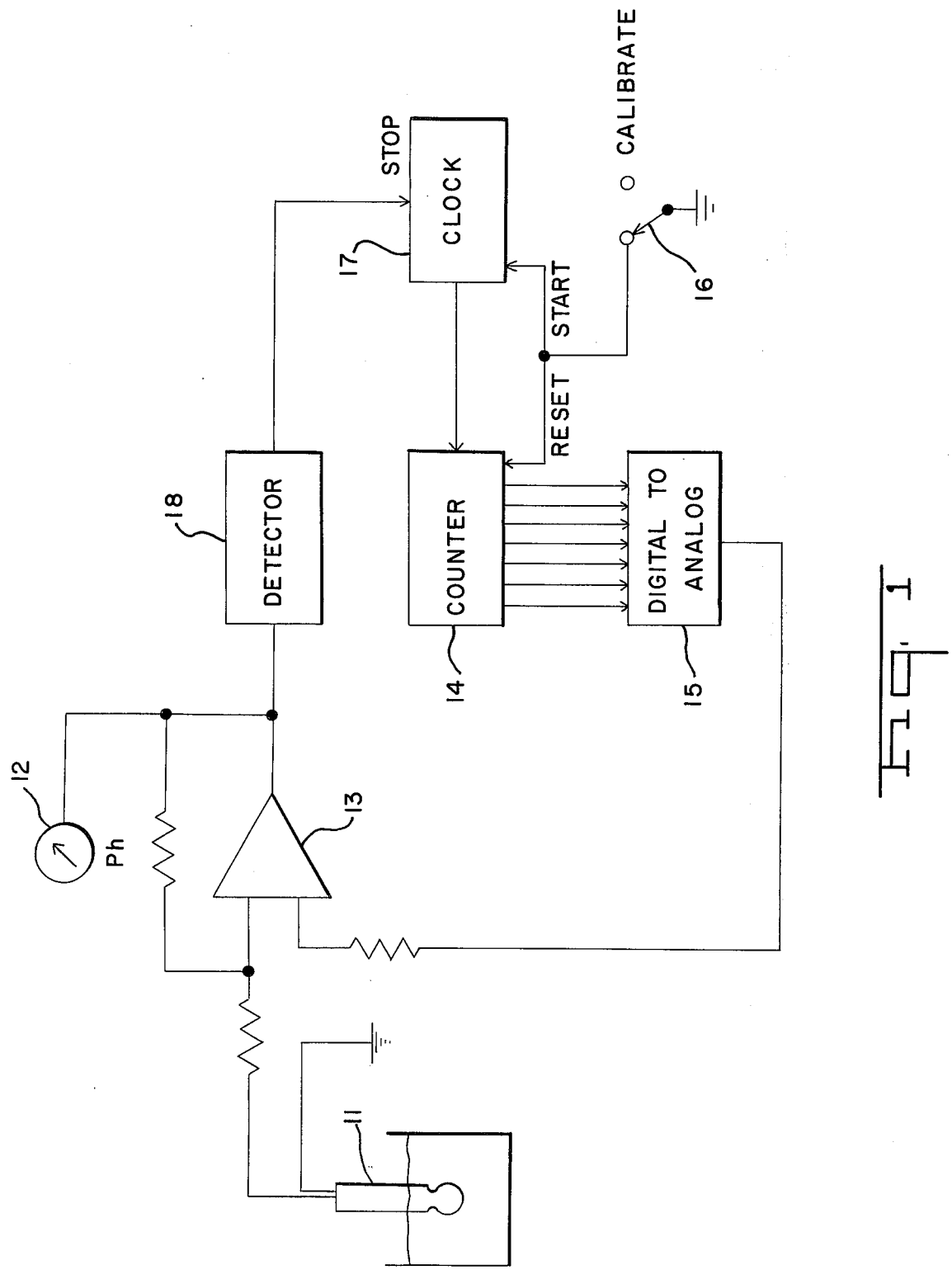
FIG. 1 is a block diagram of the calibration system.

Referring to FIG. 1 the pH measuring system includes the usual electrodes 11 which are immersed in a sample. A meter 12 registers the pH of the sample solution.

During a calibration operation the electrodes 11 are immersed in a calibrating solution which can have a pH between 5.5 and 9.5. In this calibration solution the measurement voltage from the electrodes should be zero. However, there are zero offset voltages in both the electrodes and in the electronics and these must be compensated in order to obtain a calibrated system. The measuring voltage from an electrode is applied to one input of the difference amplifier 13. A voltage which compensates for the zero offset is applied to the other input of difference amplifier 13.

This compensating voltage is generated by a counter 14 having its outputs connected to the digital-to-analog converter 15. During a calibrate operation the switch 16 is moved to the calibrate position. This resets the counter 14 and enables the clock 17 to supply clock pulses to the counter 14. As the counter 14 counts these clock pulses the digital-to-analog converter 15 produces a staircase output voltage. This staircase voltage is algebraically added to the measurement voltage from the electrode.

Figure 2B:
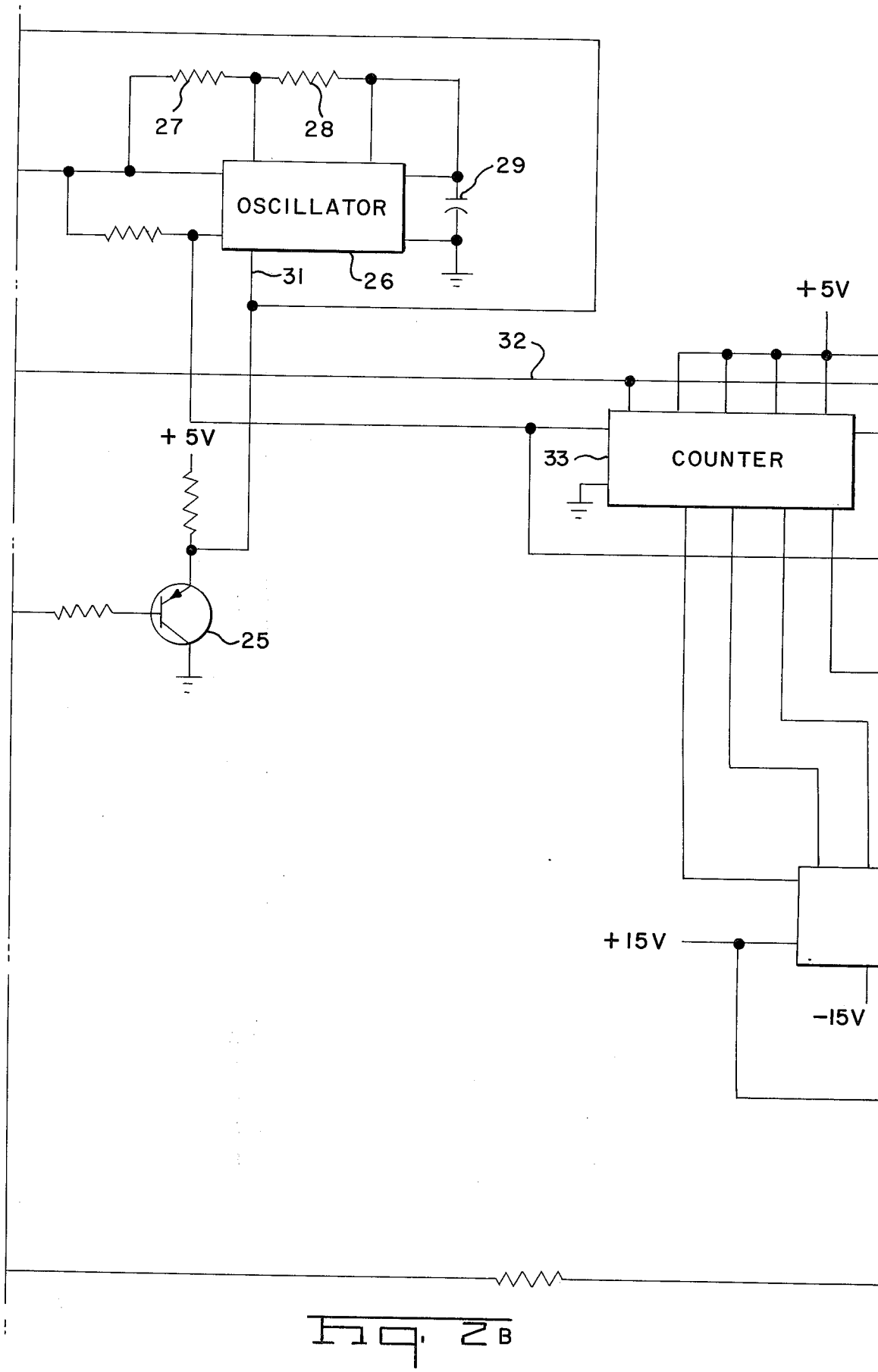
FIGS. 2A–2C together form a schematic diagram of the invention.
Figures 2, 2A:
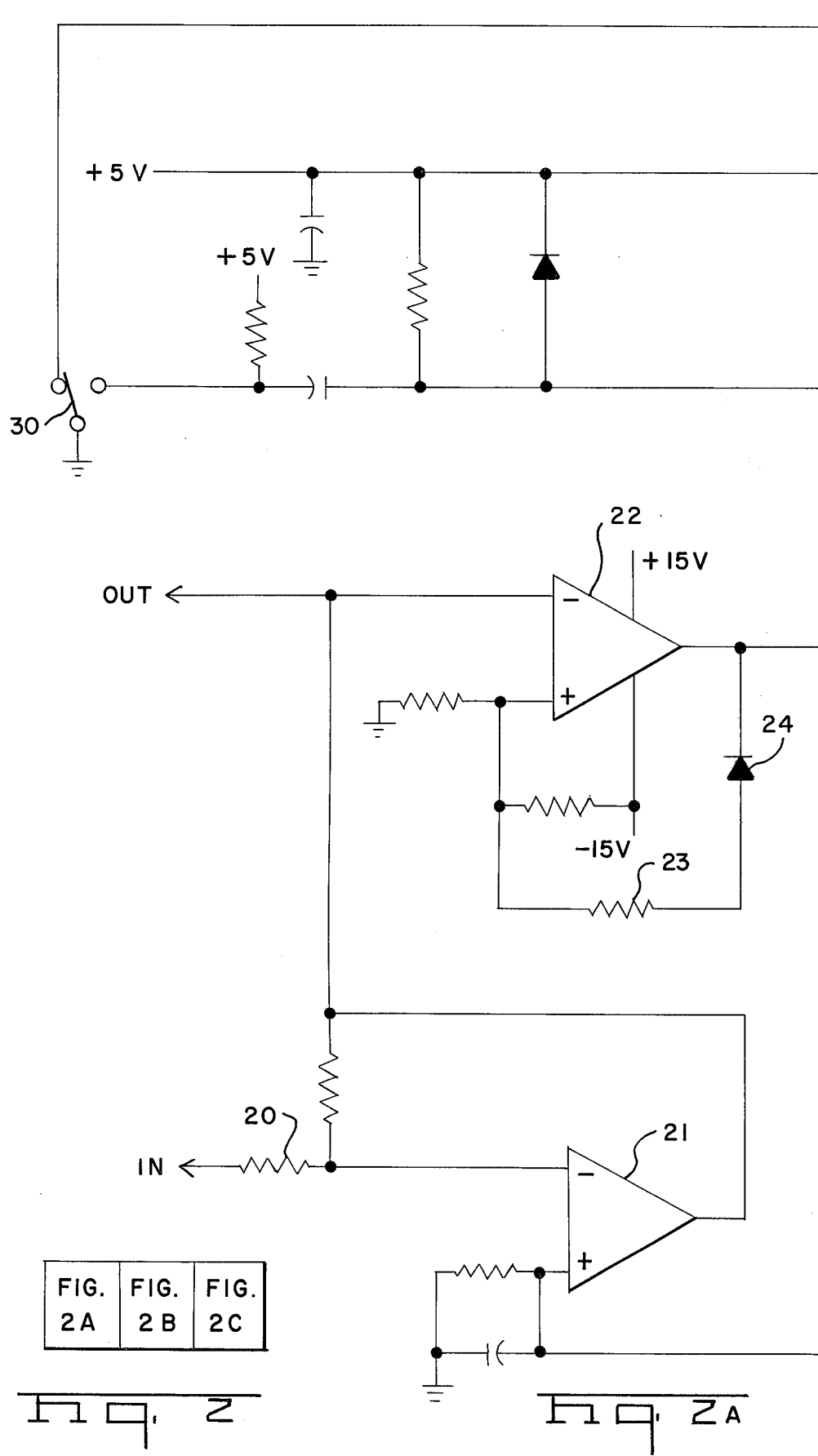
Figure 2C:
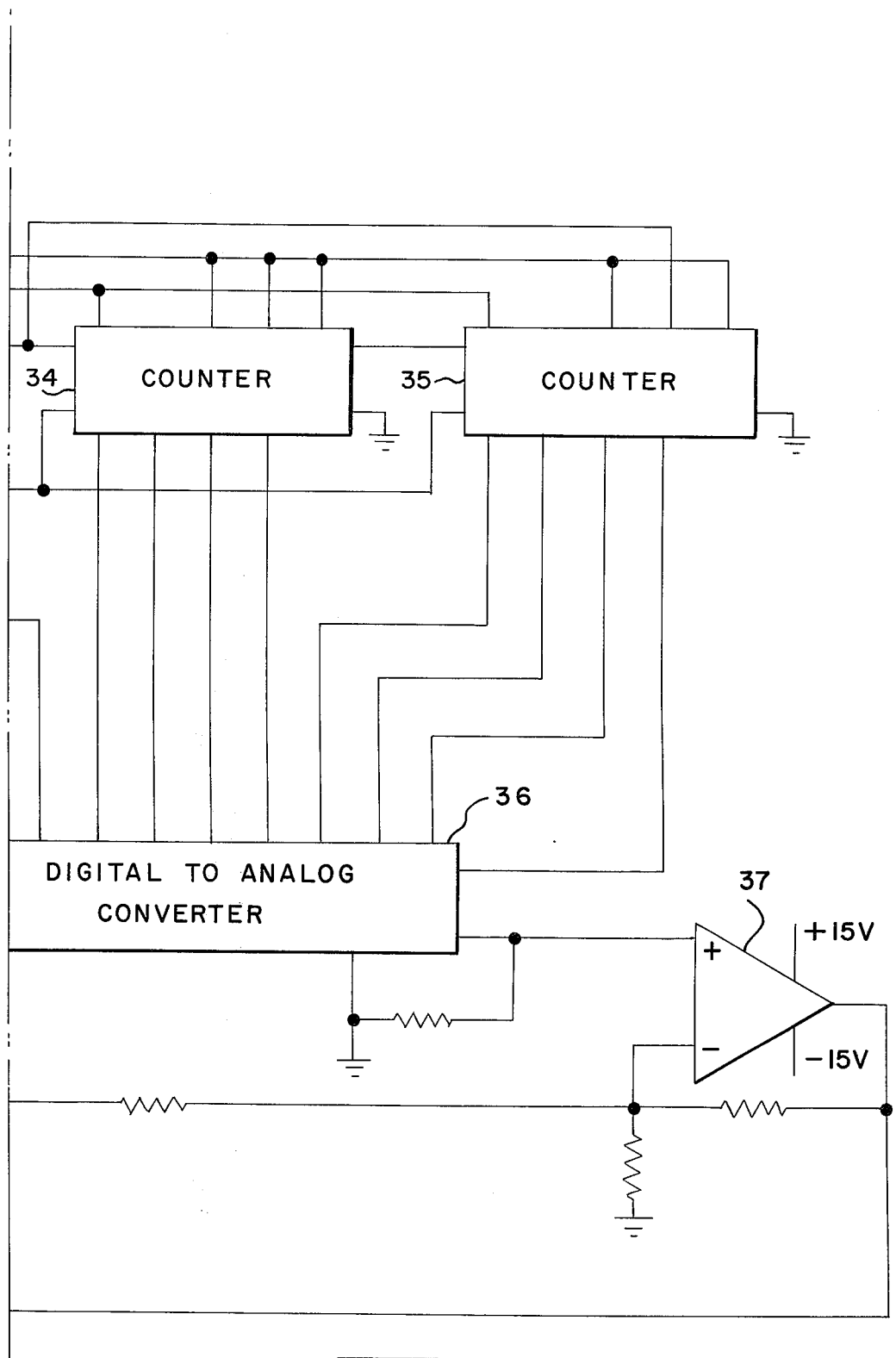

Referring to FIGS. 2A–2C, the input to the automatic calibration circuit is applied to the resistor 20. The input is the filtered output from the pH pre-amplifier. The input is applied to the inverting input of the difference amplifier 21. During the calibration operation a voltage staircase is applied to the non-inverting input of difference amplifier 21. When the algebraic sum of the input measuring signal and the staircase voltage reaches zero the calibration phase is automatically terminated.

The detector which determines when the sum reaches zero includes the difference amplifier 22. The non-inverting input of amplifier 22 is biased to −½ of the least significant bit of the staircase voltage. For example, in one embodiment of the invention the staircase voltage has a positive range of +8.5 volts. In this case the non-inverting input of amplifier 22 is biased to approximately −4.2 volts. The difference amplifier 22 stops the calibration phase when the voltage applied to the inverting input equals this predetermined voltage applied to the non-inverting input. Since the input offset voltage is uniformly distributed with respect to the staircase voltage, the detector will on the average stop at zero with a standard deviation of 0.28 of the least significant bit of the staircase voltage. For the case when the staircase voltage reaches exactly −½ of the least significant bit, hysteresis is added via resistor 23 and diode 24 to ascertain stable detection. In order to make the least significant bit stable, it is necessary to increase the resolution of the automatic circuit so that it is greater than the digital readout.

The output of the zero crossing detector is level shifted by the transistor 25 which turns off the oscillator 26. The frequency of this oscillator is determined by the resistors 27 and 28 and the capacitor 29 but the frequency is not critical.

When the calibration switch 30 is in its normal position the oscillator 26 is disabled because ground potential is applied to the input lead 31. This prevents the oscillator 26 from operating under conditions when pH measurements are being made.

To initiate a calibrate operation the switch 30 is momentarily actuated to the calibrate position. This enables the oscillator 26 and a reset pulse is applied over line 32 to the counters 33–35. Counters 33, 34 and 35 are synchronous binary counters which produce a 12 bit binary output. This 12 bit binary output is converted to the staircase voltage by digital-to-analog converter 36. The staircase voltage is amplified and level shifted in the amplifier 37.

When the binary counters 33–35 are reset, the staircase voltage starts at its lowest value. It increases in steps until it balances the voltage offset. The staircase voltage increases until the algebraic sum of the staircase voltage and the offset voltage exactly balance each other in the output of difference amplifier 21. At this time the calibration operation is terminated.

While a particular embodiment of the invention has been shown and described, various modifications are within the true spirit and scope of the invention.

What is claimed is:

1. An automatic calibration system for an electronic pH measuring system of the type which produces a measurement voltage in a predetermined range, which represents the pH of a sample being analyzed and which includes a fixed zero offset DC voltage comprising:

a first difference amplifier, said measurement voltage being applied to one input to said difference amplifier, indicating means operable over the range and connected to the output of said first difference amplifier for producing an output indication representing the pH of a sample being analyzed, said indication being corrected for said fixed zero offset DC voltage, a source of clock pulses, a counter, switch means for resetting said counter at the start of a calibration and for supplying said clock pulses to said counter during said calibration, a digital-to-analog converter having its input connected to the output of said counter, the output of said converter being connected to the other input of said difference amplifier to algebraically add said output to said measurement voltage, and a detector connected to the output of said difference amplifier for stopping the supply of clock pulses to said counter when the algebraic sum of said measurement voltage and the output of said converter reaches a predetermined level.

2. The system recited in claim 1 wherein said detector comprises:

a second difference amplifier, the output of said first difference amplifier being connected to one input of said second difference amplifier, and a source of bias voltage representing said predetermined level connected to the other input of said second difference amplifier.

* * * * *